United States Patent [19]
Zingheim

[11] Patent Number: 4,904,187
[45] Date of Patent: Feb. 27, 1990

[54] DENTAL IMPLANT
[75] Inventor: William F. Zingheim, Escondido, Calif.
[73] Assignee: Tri-Stage, Inc., Solana Beach, Calif.
[21] Appl. No.: 180,990
[22] Filed: Apr. 13, 1988
[51] Int. Cl.[4] .............................................. A61C 8/00
[52] U.S. Cl. .................................................... 433/173
[58] Field of Search ................ 433/173, 174, 175, 221
[56] References Cited
U.S. PATENT DOCUMENTS

| 2,857,670 | 10/1958 | Kiernan, Jr. | 433/175 |
|---|---|---|---|
| 3,717,932 | 2/1973 | Brainin | 433/175 |
| 4,253,833 | 3/1981 | Edelman | 433/173 |
| 4,447,209 | 5/1984 | Sutter | 433/173 |
| 4,468,200 | 8/1984 | Munch | 433/174 |
| 4,474,556 | 10/1984 | Ellis et al. | 433/173 |
| 4,479,783 | 10/1984 | Weissman | 433/221 |
| 4,723,913 | 2/1988 | Bergman | 433/173 |
| 4,758,160 | 7/1988 | Ismail | 433/173 |
| 4,826,434 | 5/1989 | Krueger | 433/174 |

Primary Examiner—Gene Mancene
Assistant Examiner—Adriene J. Lepiane
Attorney, Agent, or Firm—Nydegger & Harshman

[57] ABSTRACT

A dental device implantable in bone comprises a hollow cylinder which has an open end and a closed end with an outer surface between the ends. A plurality of shallow oblong-shaped grooves are formed into the surface near the closed end with the longitudinal axis of the grooves aligned to inhibit rotation of the device in the bone. Additionally, a shallow annular depression traversing each of the grooves is formed into the surface to inhibit vertical displacement of the device in the bone.

17 Claims, 2 Drawing Sheets

DENTAL IMPLANT

BACKGROUND OF THE INVENTION

The present invention relates to abutments implantable in bones which are useful for attaching prosthetic devices to the bone. More specifically, the present invention pertains to an implant which resists both rotation and displacement of the implant relative to the bone. The device of the present invention is particularly, but not exclusively, useful as a dental implant.

DISCUSSION OF THE PRIOR ART

The use of bone implants as abutments to which prosthetic devices can be attached is well known. Such uses are particularly common in the field of dental implantology. In this field, as well as the other fields where it is necessary to engage a prosthetic device to a bone, the object is to securely seat the implanted abutment into the bone. Specifically, the object is to securely implant the abutment so it effectively reacts as part of the bone. To a great extent, the efficacy of the implant is dependent upon the ability of the bone to adaptively seal onto the implant. Unfortunately, reliance on this bone adaptation, alone, is typically not sufficient. Thus, various attempts have been made to mechanically enhance the interaction between the bone and the implanted abutment.

As between the bone and the device implanted into the bone, the device will most likely be the stronger of the two. Therefore, it is the bone's ability to adapt to the implant and thereby withstand or resist an applied force which is of overriding concern. Where an implant is concerned, the bone can resist relative movement of the implant until it either fails in shear or fails in compression. In the former case, a fragment of the bone is broken. In the latter case, a portion of the bone is crushed. The actual amount of resistive force that must be overcome in either case will depend upon several variables.

One extremely important factor which should be taken into account when considering the interaction between an implant device and the bone is the location of stress risers. In general, stress risers are points at the interface between the implanted device and the bone where stresses will tend to concentrate and may eventually cause a catastrophic failure of the bone. Typically, stress risers occur along lines or at points on the interface between the implant device and bone where abrupt edges or protrusions of the device cause it to cut or gouge into the bone. Stress risers should be avoided or eliminated for at least two reasons. First, bones do not adapt to stress risers. Hence the strengthening effect of bone adaptation is lost at that point where the stress riser is located. Second, excessive concentrations of stress on the bone, such as are present at stress risers, cause bone demineralization and a consequent weakening of the bone.

Another important consideration for the design of an implant device concerns the nature of the force generated on the bone at the interface. It is known that any given cross-section of bone is able to resist more force in compression than it can in shear. Thus, it is clearly desirable if an implant minimizes the shear and torsional forces it exerts on a bone and, instead, causes the interaction to become compressive in nature. A greater appreciation of this can be had by considering Poisson's ratio. Additionally, it will be appreciated by the skilled artisan that bone can actually be strengthened by compressive forces.

Several currently available implant devices have attempted to benefit from the bone's resistance to shear in an effort to mechanically enhance the implant's interaction with the bone. For example, U.S. Pat. No. 4,431,416 to Niznick discloses a self-tapping screw thread and three rows of perforations about the anchor core which are intended to provide a connection between the implant and the bone. Further, U.S. Pat. No. 4,624,673 to Meyer also discloses screw threads which are intended to handle an increased loading capacity. Additionally, U.S. Pat. No. 4,657,510 to Gittleman discloses apertures and grooves which are intended to facilitate the securing of the sleeve member. All of these devices effectively challenge the bone with shearing forces. Importantly, they also establish stress risers in the bone.

Unlike the implant devices cited above, the present invention recognizes that the bone's resistance to compression is substantial and can be used to advantage. Further, the present invention recognizes that shallow elongated grooves on the surface of an implant require bone compression, rather than bone shear, before there can be relative movement therebetween. Additionally, the present invention recognizes that such grooves can be oriented on the implant to essentially eliminate stress risers and efficaciously resist both a rotational movement and a vertical displacement of the implant relative to the bone.

Accordingly, and in light of the above, it is an object of the present invention to provide an implant device which will react against the bone's resistance to compression for holding the device in the bone. It is another object of the present invention to provide an implant which will meet compressive resistance from the bone whenever there is an attempt to rotate or displace the implant relative to the bone. Still another object of the present invention is to provide an implant which effectively eliminates the adverse effects of stress risers. Yet another object of the present invention is to provide an implant which can be easily placed into a prepared site in the bone, is relatively easily manufactured and is cost effective.

SUMMARY OF THE INVENTION

A dental implant device comprises a tubular-shaped cylinder having an open end and a closed end. The outer surface of the cylinder between the open and closed ends is formed with a plurality of oblong-shaped shallow grooves which have smoothly rounded transitions between the grooves and the surface and extend longitudinally along the cylinder to inhibit rotation of the implanted device relative to the bone. An annular depression having smoothly rounded transitions is also formed into the outer surface of the cylinder. This annular depression traverses each of the grooves to inhibit vertical displacement of the implanted device relative to the bone. The closed end of the device may be either rounded or formed with a circular flat which is connected to the outer surface of the cylinder by a ramp.

A cavity extends longitudinally into the cylinder from the open end toward the closed end. The cavity is threaded for threadable engagement with prosthetic objects, such as a tooth, and is also formed with a plurality of opposed sides which present flat faces to the interior of the cavity for engagement with a tool, such as a hexagonal wrench. A raised neck may be formed around the outside of the cavity at the open end of the cylinder to help wedge the implant into a prepared site in the bone. A healing screw may be provided which is threadably engageable with the cavity to seal and close the cavity during the time following insertion of the device into a prepared site when the implant is adapting to the bone.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE FIGURES

FIG. 1A is a side elevational view of another embodiment of the device implanted in a bone;

DESCRIPTION OF THE PREFERRED EMBODIMENT

Figure 1:
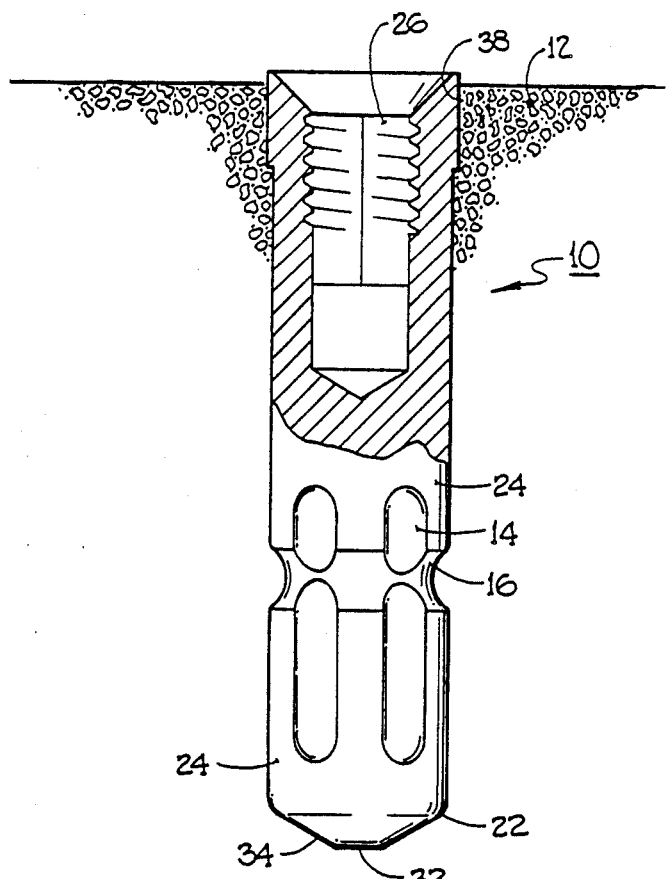
FIG. 1 is a side elevational view of the device implanted in a bone with portions broken away for clarity.

Referring initially to FIG. 1, the implant device of the present invention, generally designated 10, is shown placed into a prepared site in bone 12. Importantly, once device 10 has been implanted and bone 12 has had the opportunity to heal, elements of bone 12 will extend into grooves 14 and depression 16 of device 10.

Figure 2:
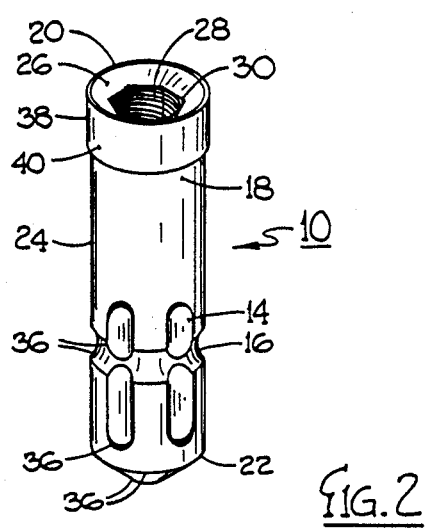
FIG. 2 is an exploded perspective view of the device with an engageable healing screw.

The structure of device 10 will perhaps be best appreciated by reference to FIG. 2 where it will be seen that device 10 is essentially a tubular-shaped cylinder 18 having an open end 20 and a closed end 22. Between ends 20 and 22 is a surface 24 which is formed with a plurality of grooves 14 and an annular depression 16. Specifically, as shown in FIG. 2, a plurality of oblong-shaped grooves 14 are formed into surface 24 of cylinder 18 with their longitudinal axes substantially parallel to the longitudinal axis of the cylinder 18. The annular-shaped depression 16 is also formed into surface 24 of cylinder 18 and traverses each groove 14. As shown, groove 14 is substantially oriented in a plane which is parallel to the longitudinal axis of cylinder 18. It will be understood that, although only one depression 16 is shown in FIGS. 1 and 2, there may be a plurality of mutually parallel depressions 16, each of which traverse grooves 14 as substantially shown in FIG. 1A.

As contemplated by the present invention, grooves 14 and depression 16 are intended to respectively inhibit rotation and vertical displacement of device 10 relative to bone 12. Further, in contemplation of the present invention, these restrictions against the movement of device 10 result from the resistance of bone 12 to compression rather than from its resistance to shear. Therefore, grooves 14 and depression 16 are preferably shallow relative to the overall dimensions of device 10. In accordance with the present invention, the depth of groove 14 from surface 24 should be approximately 0.015 inches and the length of groove 14 should be in a range between 0.12 inches and 0.32 inches. Likewise, the depth of depression 16 should be approximately 0.015 inches. Importantly, each transition 36, i.e. the change from the surface 24 to a groove 14 or from the surface 24 to a depression 16, will be smoothly rounded in order to reduce or eliminate stress risers. Further, each transition 36 defines a change in surface orientation through an arc length which is less than thirty degrees. These limitations, together with generous radii of curvature for transitions 36, effectively eliminate the abrupt angular presentations which cause stress risers in the bone.

Figure 5:
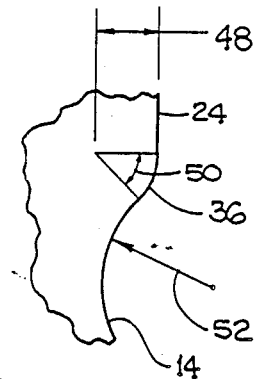
FIG. 5 is a schematic drawing of a transition on the device.

Referring for the moment to FIG. 5, a transition 36 formed as the connection between surface 24 and groove 14 is clearly shown. Recall that a transition 36 is likewise applicable between surface 24 and depression 16. As shown in FIG. 5, the radius of curvature 48 for transition 36 is preferably less than 0.005 inches. Further, angle 50 is preferably less than thirty (30) degrees. Additionally, the radius of curvature 52 for groove 14 (or depression 16) will be on the order of 0.03 inches. Within these parameters, the transition 36 can be formed as the rounded connection between surface 24 and shallow groove 14 or shallow depression 16.

Figure 3:
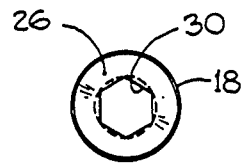
FIG. 3 is a top view of the device.

FIGS. 1 and 2 also show that device 10 is formed with a cavity 26 which extends longitudinally into cylinder 18 from open end 20 toward closed end 22. Also, cavity 26 is formed with threads 28 and a plurality of sides 30 which present a flat face to the interior of cavity 26. Sides 30 are best seen in FIG. 3 wherein it will be appreciated that the sides 30 can be arranged in opposed pairs. Specifically, FIG. 3 shows an arrangement wherein sides 30 form a hexagon which is operatively engageable with a hexagonal wrench (not shown) for manipulating device 10 into bone 12.

Figure 4:
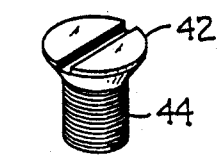
FIG. 4 is a bottom view of the device.
Figure 4:
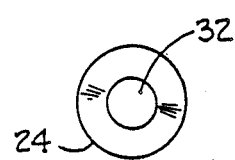

Closed end 22 may be rounded. Preferably, however, closed end 22 is formed with a circular flat 32 which is joined to surface 24 by a ramp 34. This relationship between flat 32, ramp 34 and surface 24 is best seen by cross-referencing FIG. 1 with FIG. 4.

Importantly, the transitions 36 between flat 32 and ramp 34, between ramp 34 and surface 24, between surface 24 and grooves 14, and the transition 36 between surface 24 and depression 16 should all be smoothly rounded. As contemplated by the present invention, these rounded transitions 36 emphasize and enhance the compressive action required against bone 12 to either rotate or displace an implanted device 10.

FIG. 2 also shows that cylinder 18 may be formed with a neck 38 which surrounds cavity 26 at the open end 20 of device 10. Neck 38 presents a surface 40 which is slightly raised relative to surface 24 and is, therefore, effective in establishing an interference fit between device 10 and bone 12. Neck 38 may be polished to inhibit bacterial growth thereon.

A healing screw 42 may be provided which has threads 44 that are engageable with threads 28 in cavity 26 to cover and seal cavity 26 during the healing of bone 12. It will be understood that other means may also be used for this purpose without departing from the spirit of the present invention.

When device 10 has been implanted into bone 12 and the bone 12 has healed, various prosthetic objects may be threadably engaged into cavity 26. Further, such objects may be attached to the device 10 by any other means well known in the art.

In the preferred embodiment of the present invention, device 10 is made of titanium.

While the particular dental implant as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device implantable in bone for holding objects while substantially eliminating stress risers at the interface between the bone and the implant which comprises:
    a tubular cylinder having an open end and a closed end, with an outer surface between said ends and a cavity extending longitudinally into said device from said open end toward said closed end;
    a plurality of oblong-shaped shallow grooves each of said grooves defining a rounded transition between said groove and outer surface which is rounded and has an arc length less than thirty degrees, said grooves being formed into said surface near said closed end with the longitudinal axes of said grooves aligned substantially parallel to the longitudinal axis of said cylinder to inhibit rotation of said device in said bone;
    an annular depression traversing each of said grooves and defining a transition between said depression and said outer surface which is rounded and has an arc length less than thirty degrees, said depression being formed into said surface to inhibit displacement of said device in said bone.

2. A device as cited in claim 1 wherein said depression bisects said grooves.

3. A device as cited in claim 2 further comprising a neck surrounding said cavity at said open end, said neck presenting a surface which is slightly raised relative to said outer surface of said cylinder.

4. A device as cited in claim 3 wherein said cavity is internally threaded for threadable engagement with said object.

5. A device as cited in claim 4 wherein said cavity is formed with a plurality of opposed sides, each of said sides presenting a flat face toward the interior of said cavity.

6. A device as cited in claim 5 wherein said sides form a hexagon.

7. A device as cited in claim 6 wherein said closed end is rounded.

8. A device as cited in claim 7 wherein said closed end is formed with a circular flat and a ramped surface between said flat and said outer surface.

9. A device as cited in claim 8 wherein said grooves are approximately 0.040 inches in width, 0.015 inches in depth, and from 0.12 inches to 0.32 inches in length.

10. A device as cited in claim 9 comprising a plurality of said depressions.

11. A device as cited in claim 10 further comprising a healing screw threadably engageable with said cavity.

12. A bone adaptable dental implant for substantially eliminating stress risers at the interface between the bone and the implant which comprises:
    a tubular cylinder having a smooth outer surface;
    a plurality of grooves oriented longitudinally on said cylinder, each of said grooves defining a transition between said groove and said outer surface which is rounded and has an arc length less than thirty degrees; and
    an annular depression which traverses said grooves and which defines a transition between said depression and said outer surface which is rounded and has an arc length less than thirty degrees.

13. A bone adaptable dental implant as recited in claim 12 wherein said cylinder comprises an open end and a closed end, with an outer surface between said ends and a cavity extending longitudinally into said implant from said open end toward said closed end.

14. A bone adaptable dental implant as recited in claim 13 further comprising a neck surrounding said cavity at said open end, said neck presenting a surface which is slightly raised relative to said outer surface of said cylinder.

15. A device as cited in claim 14 wherein said closed end is rounded.

16. A device as cited in claim 14 wherein said closed end is formed with a circular flat and a ramped surface between said flat and said outer surface.

17. A device as cited in claim 14 wherein said grooves are approximately 0.040 inches in width, 0.015 inches in depth, and from 0.12 inches to 0.32 inches in length.

* * * * *